(12) United States Patent
Shome et al.

(10) Patent No.: US 9,020,596 B2
(45) Date of Patent: Apr. 28, 2015

(54) MANAGEMENT OF FUSION BEAT DETECTION DURING CAPTURE THRESHOLD DETERMINATION

(75) Inventors: Shibaji Shome, Arden Hills, MN (US); Yanting Dong, Lexington, KY (US); Aaron R. McCabe, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 39 days.

(21) Appl. No.: 13/546,820

(22) Filed: Jul. 11, 2012

(65) Prior Publication Data

US 2013/0018433 A1 Jan. 17, 2013

Related U.S. Application Data

(60) Provisional application No. 61/508,443, filed on Jul. 15, 2011.

(51) Int. Cl.
 *A61N 1/37* (2006.01)
(52) U.S. Cl.
 CPC ................... *A61N 1/3712* (2013.01)
(58) Field of Classification Search
 USPC .......................................................... 607/28
 See application file for complete search history.

(56) References Cited

U.S. PATENT DOCUMENTS

| 4,832,041 A | 5/1989 | Wang et al. |
| 4,895,152 A | 1/1990 | Callaghan et al. |
| 5,273,049 A | 12/1993 | Steinhaus et al. |
| 5,312,445 A | 5/1994 | Nappholz et al. |
| 5,330,511 A | 7/1994 | Boute |
| 5,331,966 A | 7/1994 | Bennett et al. |
| 5,334,220 A | 8/1994 | Sholder |
| 5,340,361 A | 8/1994 | Sholder |
| 5,350,410 A | 9/1994 | Kleks et al. |
| 5,391,192 A | 2/1995 | Lu et al. |
| 5,431,691 A | 7/1995 | Snell et al. |
| 5,458,623 A | 10/1995 | Lu et al. |
| 5,534,016 A | 7/1996 | Boute |
| 5,540,727 A | 7/1996 | Tockman et al. |
| 5,626,623 A | 5/1997 | Kieval et al. |
| 5,660,184 A | 8/1997 | Donehoo et al. |
| 5,674,254 A | 10/1997 | van Krieken |
| 5,741,308 A | 4/1998 | Sholder |

(Continued)

FOREIGN PATENT DOCUMENTS

| EP | 1123716 | 8/2001 |
| EP | 1155711 | 11/2001 |

(Continued)

OTHER PUBLICATIONS

"U.S. Appl. No. 10/003,718, Final Office Action mailed Sep. 13, 2005", 6 pgs.

(Continued)

*Primary Examiner* — Joseph Dietrich
(74) *Attorney, Agent, or Firm* — Schwegman Lundberg & Woessner, P.A.

(57) ABSTRACT

An improved technique is described for dealing with the detection of fusion beats when capture verification is performed by a cardiac pacing device such as during a capture threshold determination procedure. Schemes for classifying heart beats may misclassify beats as fusion beats due to feature/morphology changes in the test electrogram waveform that may occur even when capture is achieved.

12 Claims, 3 Drawing Sheets

(56) References Cited

U.S. PATENT DOCUMENTS

| | | | |
|---|---|---|---|
| 5,755,739 | A | 5/1998 | Sun et al. |
| 5,771,898 | A | 6/1998 | Marinello |
| 5,778,881 | A | 7/1998 | Sun et al. |
| 5,782,888 | A | 7/1998 | Sun et al. |
| 5,817,134 | A | 10/1998 | Greenhut et al. |
| 6,029,088 | A | 2/2000 | Budgifvars et al. |
| 6,101,416 | A | 8/2000 | Sloman |
| 6,128,535 | A | 10/2000 | Maarse |
| 6,169,921 | B1 | 1/2001 | KenKnight et al. |
| 6,253,102 | B1 | 6/2001 | Hsu et al. |
| 6,304,773 | B1 | 10/2001 | Taylor et al. |
| 6,418,340 | B1 | 7/2002 | Conley et al. |
| 6,456,881 | B1 | 9/2002 | Bornzin et al. |
| 6,512,953 | B2 | 1/2003 | Florio et al. |
| 6,609,023 | B1 | 8/2003 | Fischell et al. |
| 6,697,673 | B1 | 2/2004 | Lu |
| 6,738,669 | B1 | 5/2004 | Sloman et al. |
| 6,829,505 | B2 | 12/2004 | Kramer et al. |
| 6,832,112 | B1 | 12/2004 | Bornzin |
| 6,865,422 | B1 | 3/2005 | Sloman et al. |
| 7,113,823 | B2 | 9/2006 | Yonce et al. |
| 7,181,284 | B2 | 2/2007 | Burnes et al. |
| 7,203,543 | B2 | 4/2007 | Meyer et al. |
| 7,286,876 | B2 | 10/2007 | Yonce et al. |
| 7,353,061 | B2 | 4/2008 | Hedberg et al. |
| 7,412,287 | B2 | 8/2008 | Yonce et al. |
| 7,555,340 | B2 | 6/2009 | Dong et al. |
| 7,558,628 | B2 | 7/2009 | Yonce et al. |
| 7,676,267 | B2 | 3/2010 | Kim et al. |
| 7,920,920 | B1 * | 4/2011 | Williamson .............. 607/28 |
| 8,078,276 | B2 | 12/2011 | Dong et al. |
| 8,116,866 | B2 | 2/2012 | Yonce et al. |
| 2001/0049542 | A1 | 12/2001 | Florio et al. |
| 2001/0049543 | A1 | 12/2001 | Kroll |
| 2002/0095183 | A1 * | 7/2002 | Casset et al. .............. 607/4 |
| 2002/0161307 | A1 | 10/2002 | Yu et al. |
| 2002/0193696 | A1 | 12/2002 | Hsu et al. |
| 2003/0083700 | A1 | 5/2003 | Hill |
| 2003/0083710 | A1 | 5/2003 | Ternes et al. |
| 2003/0083711 | A1 | 5/2003 | Yonce et al. |
| 2004/0088018 | A1 | 5/2004 | Sawchuk et al. |
| 2004/0158165 | A1 | 8/2004 | Yonce et al. |
| 2004/0158293 | A1 | 8/2004 | Yonce et al. |
| 2004/0215249 | A1 | 10/2004 | Corbucci |
| 2004/0215252 | A1 | 10/2004 | Verbeek et al. |
| 2005/0038478 | A1 | 2/2005 | Klepfer et al. |
| 2005/0131476 | A1 | 6/2005 | Kim et al. |
| 2005/0209649 | A1 | 9/2005 | Ferek-petric |
| 2005/0209650 | A1 | 9/2005 | Van Gelder et al. |
| 2007/0162082 | A1 | 7/2007 | Ternes et al. |
| 2007/0219593 | A1 | 9/2007 | Yonce et al. |
| 2008/0228093 | A1 | 9/2008 | Dong et al. |
| 2010/0016920 | A1 | 1/2010 | Hahn et al. |
| 2010/0023082 | A1 | 1/2010 | Dong et al. |

FOREIGN PATENT DOCUMENTS

| | | |
|---|---|---|
| WO | WO-03020366 A1 | 3/2003 |
| WO | WO-03022148 A1 | 3/2003 |
| WO | WO-03037428 A2 | 5/2003 |
| WO | WO-2004026398 A1 | 4/2004 |
| WO | WO-2005053792 A1 | 6/2005 |

OTHER PUBLICATIONS

"U.S. Appl. No. 10/003,718, Non Final Office Action mailed Mar. 22, 2006", 5 pgs.

"U.S. Appl. No. 10/003,718, Non-Final Office Action mailed Sep. 30, 2004", 5 pgs.

"U.S. Appl. No. 10/003,718, Notice of Allowance mailed Sep. 27, 2006", 6 pgs.

"U.S. Appl. No. 10/003,718, Response filed Jan. 13, 2006 to Final Office Action mailed Sep. 13, 2005", 9 pgs.

"U.S. Appl. No. 10/003,718, Response filed Apr. 12, 2004 to Restriction Requirement mailed Mar. 11, 2004", 10 pgs.

"U.S. Appl. No. 10/003,718, Response filed Jul. 24, 2006 to Non Final Office Action mailed Mar. 22, 2006", 11 pgs.

"U.S. Appl. No. 10/003,718, Response filed Dec. 30, 2004 to Non Final Office Action mailed Sep. 30, 2004", 10 pgs.

"U.S. Appl. No. 10/003,718, Restriction Requirement mailed Mar. 11, 2004", 5 pgs.

"U.S. Appl. No. 10/251,629, Appeal Brief filed Oct. 23, 2006", 24 pgs.

"U.S. Appl. No. 10/251,629, Restriction Requirement mailed Jun. 28, 2005", 5 pgs.

"U.S. Appl. No. 10/251,629, Final Office Action mailed Mar. 22, 2006", 9 pgs.

"U.S. Appl. No. 10/251,629, Non Final Office Action mailed Oct. 13, 2005", 7 pgs.

"U.S. Appl. No. 10/251,629, Notice of Allowance mailed Feb. 20, 2007", 4 pgs.

"U.S. Appl. No. 10/251,629, Response filed Feb. 13, 2006 to Non Final Office Action mailed Oct. 13, 2005", 11 pgs.

"U.S. Appl. No. 10/251,629, Response filed Jul. 28, 2005 to Restriction Requirement mailed Jun. 28, 2005", 9 pgs.

"U.S. Appl. No. 10/723,254, Advisory Action mailed Jan. 9, 2007", 3 pgs.

"U.S. Appl. No. 10/723,254, Final Office Action mailed Jul. 15, 2008", 7 pgs.

"U.S. Appl. No. 10/723,254, Final Office Action mailed Oct. 6, 2006", 7 pgs.

"U.S. Appl. No. 10/723,254, Final Office Action mailed Oct. 9, 2007", 7 pgs.

"U.S. Appl. No. 10/723,254, Non-Final Office Action mailed Jan. 7, 2008", 8 pgs.

"U.S. Appl. No. 10/723,254, Non-Final of Action mailed Feb. 16, 2007", 6 pgs.

"U.S. Appl. No. 10/723,254, Non-Final Office Action mailed Apr. 26, 2006", 6 pgs.

"U.S. Appl. No. 10/723,254, Response filed Jul. 16, 2007 to Non Final office action mailed Feb. 16, 2007", 8 pgs.

"U.S. Appl. No. 10/723,254, Response filed Jul. 26, 2006 to Non Final office action mailed Apr. 26, 2006", 7 pgs.

"U.S. Appl. No. 10/723,254, Response filed Oct. 30, 2007 to Final Office Action mailed Oct. 9, 2007", 8 pgs.

"U.S. Appl. No. 10/723,254, Response filed Dec. 6, 2006 to Final office action mailed Oct. 6, 2006", 6 pgs.

"U.S. Appl. No. 10/723,254 Response filed Apr. 7, 2008 to Non-Final Office Action mailed Jan. 7, 2008", 8 pgs.

"U.S. Appl. No. 10/723,255, Non Final Office Action mailed Nov. 30, 2005", 5 pgs.

"U.S. Appl. No. 10/723,255, Notice of Allowance mailed Mar. 22, 2006", 4 pgs.

"U.S. Appl. No. 10/723,255, Notice of Allowance mailed Jun. 2, 2005", 6 pgs.

"U.S. Appl. No. 10/723,255, Response filed Feb. 2, 2006 to Non Final Office Action mailed Nov. 30, 2005", 8 pgs.

"U.S. Appl. No. 10/744,911, Final Office Action mailed Dec. 15, 2006", 7 pgs.

"U.S. Appl. No. 10/744,911, Non Final office action mailed Mar. 2, 2006", 8 pgs.

"U.S. Appl. No. 10/744,911, Notice of Allowance mailed Jan. 25, 2008", 6 pgs.

"U.S. Appl. No. 10/744,911, Response filed Mar. 15, 2007 to Final office action mailed Dec. 15, 2006", 13 pgs.

"U.S. Appl. No. 10/744,911 Response filed Jun. 30, 2006 to Non Final office action mailed Mar. 2, 2006", 12 pgs.

"U.S. Appl. No. 11/097,460, Non-Final Office Action with Restriction Requirement mailed Apr. 17, 2008", 15 pgs.

"U.S. Appl. No. 11/097,460, Notice of Allowance mailed Mar. 6, 2009", 6 pgs.

"U.S. Appl. No. 11/097,460, Notice of Allowance mailed Nov. 10, 2008", 7 pgs.

"U.S. Appl. No. 11/097,460, Response filed Jul. 17, 2008 to Non Final Office Action mailed Apr. 17, 2008", 12 pgs.

(56) References Cited

OTHER PUBLICATIONS

"U.S. Appl. No. 11/456,485, Notice of Allowance mailed Mar. 9, 2009", 6 pgs.
"U.S. Appl. No. 11/456,485, Notice of Allowance mailed Nov. 10, 2008", 12 pgs.
"U.S. Appl. No. 11/620,901, Appeal Brief Under 37 C.F.R. filed Jun. 7, 2012", 20 pgs.
"U.S. Appl. No. 11/620,901, Decision on Pre-Appeal Brief mailed May 7, 2012", 2 pgs.
"U.S. Appl. No. 11/620,901, Final Office Action mailed Oct. 11, 2011", 9 pgs.
"U.S. Appl. No. 11/620,901, Non FinalOffice Action mailed Mar. 18, 2011", 8 pgs.
"U.S. Appl. No. 11/620,901, Response filed Jan. 7, 2011 to Non Final Office Action mailed Oct. 7, 2010", 9 pgs.
"U.S. Appl. No. 11/620,901, Response filed Jul. 18, 2011 to Non Final Office Action mailed Mar. 18, 2011", 9 pgs.
"U.S. Appl. No. 11/754,496 Non-Final Office Action mailed Oct. 7, 2010", 6 pgs.
"U.S. Appl. No. 11/754,496, Final Office Action mailed Apr. 6, 2011", 8 pgs.
"U.S. Appl. No. 11/754,496, Non Final Office Action mailed Jun. 29, 2012", 9 pgs.
"U.S. Appl. No. 11/754,496, Response filed Jan. 7, 2011 to Non Final Office Action mailed Oct. 7, 2010", 11 pgs.
"U.S. Appl. No. 12/494,628, Non Final Office Action mailed Apr. 13, 2011", 5 pgs.
"U.S. Appl. No. 12/494,628, Notice of Allowance mailed Aug. 15, 2011", 5 pgs.
"U.S. Appl. No. 12/494,628, Response filed Jul. 13, 2011 to Non Final Office Action mailed Apr. 13, 2011", 8 pgs.
"U.S. Appl. No. 12/498,188, Response filed Sep. 15, 2011 to Non Final Office Action mailed Jun. 15, 2011", 5 pgs.
"U.S. Appl. No. 12/498,188, Non Final Office Action mailed Jun. 15, 2011", 5 pgs.
"U.S. Appl. No. 12/498,188, Notice of Allowance mailed Oct. 12, 2011", 5 pgs.
"U.S. Appl. No. 12/498,188, Response filed May 19, 2011 to Restriction Requirement mailed Apr. 19, 2011", 9 pgs.
"U.S. Appl. No. 12/498,188, Restriction Requirement mailed Apr. 19, 2011", 5 pgs.
"International Application Serial No. PCT/U503/29181, International Search Report mailed Jan. 28, 2004", 7 pgs.
"Japanese Application Serial No. 2004-537888, Notice of Reasons for Rejection mailed Aug. 31, 2009", 8 pgs.
"Pre-Appeal Brief Request for Review filed Aug. 8, 2011", Pre-Appeal Brief Request for Review, 5 pgs.
Dong, Yanting, et al., "Adjusting Cardiac Pacing Response Sensing Intervals", U.S. Appl. No. 13/306,611, filed Nov. 29, 2011, 73 pgs.

\* cited by examiner

MANAGEMENT OF FUSION BEAT DETECTION DURING CAPTURE THRESHOLD DETERMINATION

CLAIM OF PRIORITY

This application claims the benefit of priority under 35 U.S.C. §119(e) of U.S. Provisional Patent Application Ser. No. 61/508,443, filed on Jul. 15, 2010, which is herein incorporated by reference in its entirety.

FIELD OF THE INVENTION

This invention pertains to devices and methods for cardiac rhythm management. In particular, the invention relates to devices and methods for delivering cardiac pacing pulses and detecting capture by the pacing pulses.

BACKGROUND

Implantable cardiac pacemakers are a class of cardiac rhythm management devices that provide electrical stimulation in the form of pacing pulses to selected chambers of the heart. (As the term is used herein, a pacemaker is any cardiac rhythm management device with a pacing functionality regardless of any additional functions it may perform such as cardioversion defibrillation.) Pacemakers typically have a programmable electronic controller that causes the pacing pulses to be output in response to lapsed time intervals and sensed electrical activity (i.e., intrinsic heart beats). Most pacemakers are programmed to operate in a so-called demand mode (a.k.a., synchronous mode), where a pacing pulse is delivered to a heart chamber during a cardiac cycle only when no intrinsic beat by the chamber is detected. An escape interval is defined for each paced chamber, which is the minimum time interval in which a beat must be detected before a pace will be delivered. The ventricular escape interval thus defines the minimum rate at which the pacemaker will allow the heart to beat, sometimes referred to as the lower rate limit. If functioning properly, the pacemaker in this manner makes up for a heart's inability to pace itself at an appropriate rhythm. Pacemakers have been developed which provide electrical pacing stimulation to one or both of the atria and/or ventricles during a cardiac cycle in an attempt to improve the coordination of atrial and/or ventricular contractions, termed cardiac resynchronization therapy. To optimize the cardiac output for some heart failure patients, for example, the right and left ventricles are paced synchronously with a determined time offset, termed biventricular pacing.

DETAILED DESCRIPTION

Figure 1:
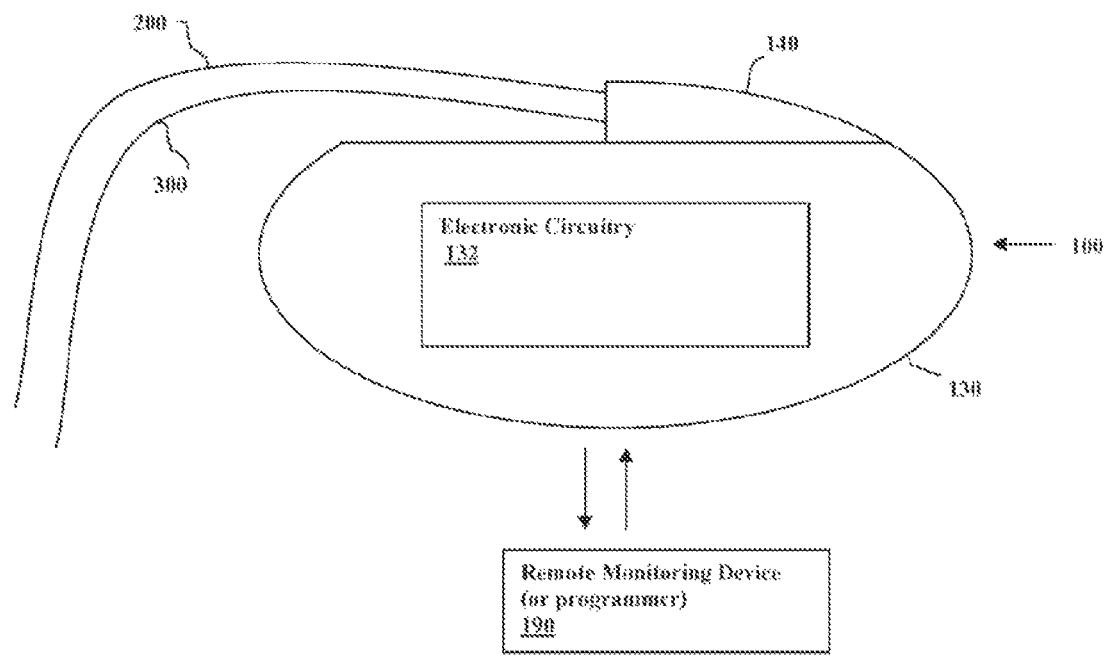
FIG. 1 shows the components of an example cardiac pacing device.

In order for a pacemaker to control the heart rate in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a demand pacemaker that is not achieving capture is not performing its function in enforcing a minimum heart rate. A number of factors can determine whether a given pacing pulse will achieve capture, but the principal factor of concern here is the energy of the pulse, which is a function of the pulse's amplitude and duration. The minimum pacing pulse energy necessary to achieve capture by a particular pacing channel is referred to as the capture threshold. Programmable pacemakers enable the amplitude and pulse width of pacing pulses to be adjusted, along with other parameters. It is common practice to determine the capture threshold by initially pacing with a high energy to ensure capture and then progressively lowering the pacing pulse energy during a sequence of cardiac cycles until capture is no longer achieved. The pacing pulse energy can then be adjusted to an appropriate value in accordance with the determined capture threshold by setting it equal to the capture threshold plus a specified safety margin.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting whether an evoked atrial or ventricular depolarization waveform exhibits one or more specified features (e.g., a peak that exceeds a specified amplitude value), the pacemaker is able to detect whether the pacing pulse (A-pulse or V-pulse) was effective in capturing the heart to result in a contraction in the respective heart chamber. Capture verification can be performed in the clinical setting, with the clinician adjusting pacing parameters so that the heart is reliably paced. It is desirable, however, for the pacemaker itself to be configured with the capability of performing this procedure in order to adapt to changing patient conditions or device behavior. In addition to performing the capture threshold determination procedure, a pacemaker may also be configured to perform capture verification during delivery of pacing therapy. When loss of capture is detected, pacing parameters can be adjusted automatically and/or a backup safety pace delivered, a function known as autocapture. (See, e.g., U.S. Pat. No. 6,169,921 assigned to Cardiac Pacemakers, Inc. and hereby incorporated by reference.) An autocapture function provides the pacemaker with extended longevity, greater ease of use, and greater patient safety.

Verification of capture by a pacing pulse as performed by a cardiac pacing device involves delivering a pacing pulse to a cardiac site and then analyzing a test electrogram recorded after delivery of the pacing pulse to determine if capture by the pacing pulse has occurred. Typically, a cardiac device records the test electrogram after a specified blanking interval subsequent to the pacing pulse during which the sensing amplifiers are blanked in order to prevent saturation of the sensing amplifiers and to allow dissipation of after-potentials on the sensing electrodes. A capture verification procedure is then performed by the device controller that may include, for example, determining whether or not the test electrogram waveform exhibits a peak amplitude within a specified range that occurs within a specified time window following delivery of the pacing pulse. These criteria may be referred to as an amplitude criterion and a location criterion, respectively. The capture verification algorithm may also include other types of feature extraction and analysis to provide greater specificity and/or sensitivity (see, e.g., U.S. Patent Application Publication No. 20050131476, hereby incorporated by reference).

During a voltage step-down pacing test for determining the capture threshold, the device progressively lowers the pacing energy while performing the capture verification procedure until the minimum pacing pulse energy that achieves capture is found. The pacing energy may then set to that minimum value plus a specified safety margin. The result of the capture verification procedure may be to classify the test electrogram as representing a capture beat or a non-capture beat (e.g., asystole) according to whether the test electrogram satisfies criteria for those classifications. Beats that do not satisfy capture or non-capture criteria may be further classified as fusion/unknown beats that occur when a paced beat fuses with an intrinsic beat or with a premature ventricular contraction. Classification of a beat as a fusion beat may also require the test electrogram to meet one or more additional criteria such as a peak with a specified amplitude range occurring within a specified time window. As such fusion beats do not represent complete capture by a pacing pulse, they cannot be used by the capture threshold determination procedure as representing either capture or non-capture. One way to reduce the occurrence of fusion beats during a capture threshold determination procedure is to increase the pacing rate so that pacing pulses are delivered before any intrinsic activation occurs. There is a limit, however, to how high the pacing rate may be safely set, and premature ventricular contractions can still occur. One strategy for dealing with this problem during a capture threshold determination test is to maintain the pacing voltage on detecting fusion beats and continue delivering pacing pulses at that voltage until capture is detected before continuing with the step down test. If fusion beats continue to occur (e.g., some specified number of fusion beats), then the test is aborted to be retried again.

Described herein is an improved way to deal with the detection of fusion beats when capture verification is performed by a cardiac pacing device such as during a capture threshold determination procedure. Schemes for classifying heart beats such as described above may misclassify beats as fusion beats due to feature/morphology changes in the test electrogram waveform that may occur even when capture is achieved. One phenomenon that may be responsible for such misclassification of capture beats as fusion beats is a pacing voltage dependent voltage shift where the peak amplitude of the test electrogram increases with decreasing pacing energy. During a capture threshold determination test, such a voltage shift may cause the test electrogram of an actual capture beat to fail to meet the amplitude criterion of the capture verification procedure even while meeting the location criterion. As a result, the beat is misclassified as a fission beat. Another scenario that may occur involves the phenomena of double peaks in the evoked response waveform. Such double peaks may be exhibited occasionally in test electrograms of actual capture beats and again cause misclassification of a capture beat as a fusion beat. Here, the amplitude criterion is met, but the location criterion is not met due to the additional peak in the waveform. The capture verification procedure may be improved by configuring the pacing device to determine whether at least the amplitude or location criterion, but not both, is consistently met by beats that would otherwise be classified as fusion beats. When this situation is detected, the beats can be regarded as misclassified fusion beats in order to allow a capture threshold determination test to continue rather than being aborted. The device may also be configured to respond to the misclassification by modifying particular parameters. For example, if a pacing voltage dependent voltage shift in the test electrogram is detected, blanking/recharge parameters that define the blanking interval may be modified and/or the ceiling of capture detection window (CDW) that defines the amplitude criterion for capture detection may be changed. If the test electrogram exhibits a double peak, the width of the CDW width may be adjusted to accommodate double peak. The height of the CDW may be constrained to mitigate the effects of the width change. The updated parameters may be utilized in the future tests throughout the test, or the parameters may be changed only for certain voltages during the capture threshold determination procedure. Additionally, the device may be configured to evaluate different combinations of sensing electrodes in the evoked response sensing channel to determine if a sensing vector can be found that eliminates the phenomenon responsible for fusion beat misclassification (e.g., a double peak).

Described below is an example cardiac device that may be configured to perform the procedures described above for capture verification during autocapture or a capture threshold determination procedure. Example embodiments are also described.

Hardware Description

Implantable pacing devices are typically placed subcutaneously or submuscularly in a patient's chest with leads threaded intravenously into the heart to connect the device to electrodes disposed within a heart chamber that are used for sensing and/or pacing of the chamber. A programmable electronic controller causes the pacing pulses to be output in response to lapsed time intervals and/or sensed electrical activity (i.e., intrinsic heart beats not as a result of a pacing pulse). FIG. 1 shows the components of an implantable pacing device 100 that includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190.

Figure 2:
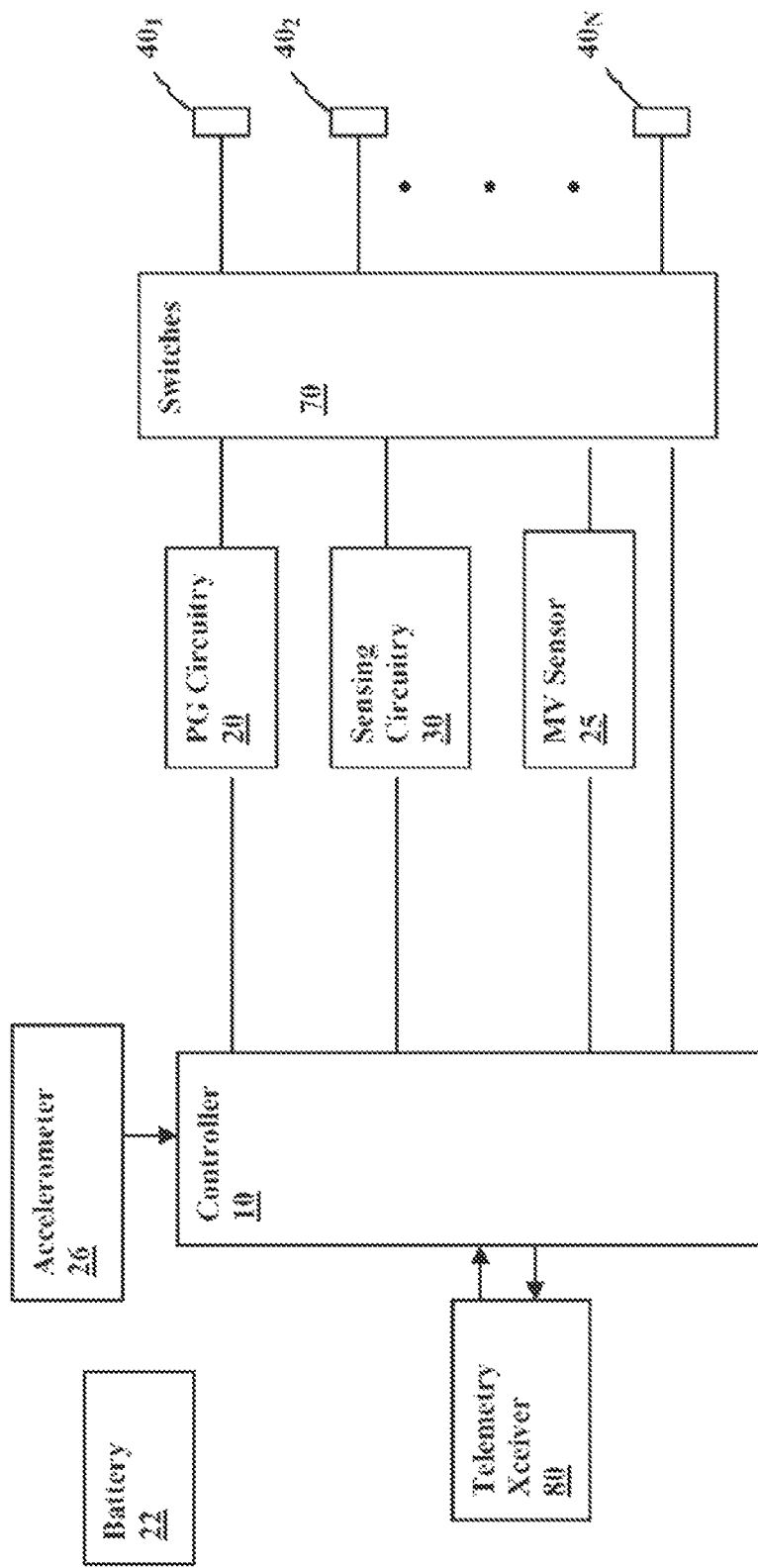
FIG. 2 is a block diagram of the electronic circuitry of an example device.

A block diagram of the circuitry 132 is illustrated in FIG. 2. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASICs (e.g., finite state machines), or implemented as a combination thereof. As the term is used herein, the programming of the controller refers to either code executed by a microprocessor or to specific configurations of hardware components for performing particular functions. The controller may be programmed to perform the procedures for capture verification and capture threshold determination as described herein.

A telemetry transceiver 80 is interfaced to the controller which enables the controller to communicate with an external programmer and/or a remote monitoring unit. Sensing circuitry 30 and pacing or pulse generation circuitry 20 are interfaced to the controller by which the controller interprets sensing signals and controls the delivery of pacing pulses in accordance with a pacing mode. The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The pulse generation circuitry 20 delivers pacing pulses to pacing electrodes disposed in the heart and includes capacitive discharge pulse generators, registers for controlling the pulse generators, and registers for adjusting pacing parameters such as pulse energy (e.g., pulse amplitude and width). The pulse generation circuitry may also include a shocking pulse generator for delivering a defibrillation/cardioversion shock via a shock electrode upon detection of a tachyarrhythmia.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads or the device housing 130 and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The switch matrix 70 allows selected ones of the available implanted electrodes to be incorporated into sensing and/or pacing channels in either unipolar or bipolar configurations that may be either atrial or ventricular channels depending upon the location of the electrode. An evoked response sensing channel may also be formed by the switch matrix for recording a test electrogram after delivery of a pacing pulse in order to determine if capture has occurred. Such an evoked response sensing channel may utilize the same electrodes used to deliver the pacing pulse or different electrodes.

The example device is also equipped with a minute ventilation sensor 25 for measuring the patient's minute ventilation and an activity level sensor 26. In rate-adaptive pacing, the pacemaker uses the sensed minute ventilation and/or the accelerometer signal to adjust the rate at which the pacemaker paces the heart in the absence of a faster intrinsic rhythm.

Example Embodiments

An example cardiac pacing device is equipped with pulse generation circuitry and sensing circuitry that may be connected to electrodes to form a pacing channel and an evoked response sensing channel. The device controller is programmed to deliver a pacing pulse to a cardiac site, record a test electrogram after delivery of the pacing pulse, and classify the test electrogram as representing a capture beat, a fusion beat, or a non-capture beat. In one embodiment, the controller is programmed to classify the test electrogram as representing: 1) a capture beat if at least an amplitude criterion that specifies a peak amplitude and a location criterion that specifies a time window within which the peak amplitude must occur are both met, 2) a fusion beat if at least one of the amplitude criterion or the location criterion is not met, and 3) a capture beat if at least one of the amplitude and location criteria is met and a predetermined number of immediately preceding test electrograms have been classified as representing fusion beats. The predetermined number may be any number found to give the best performance and may be set to zero so that the modified capture detection criteria are applied to all beats.

In other embodiments, if only one of the amplitude and location criteria is met and a predetermined number of immediately preceding test electrograms have been classified as representing fusion beats, the device is programmed to: 1) adjust a blanking/recharge parameter used to define a blanking interval for a sensing channel used to record the test electrogram, 2) modify the amplitude criterion, 3) decrease the amplitude criterion, and/or 4) increase the width of the time window specified by the location criterion. In another embodiment, the device may be programmed such that if: 1) the test electrogram exhibits a double peak, 2) only one of the amplitude and location criteria is met, and 3) a predetermined number of immediately preceding test electrograms have been classified as representing fusion beats, the width of the time window specified by the location criterion is increased to encompass the double peak. In another embodiment, to reclassify the fusion beats to capture beats, a predetermined number of immediately preceding test electrograms that are classified as fusion beats need to have similar peak timings and amplitudes. In yet another embodiment, instead of taking in account of only immediately preceding testing electrograms, the electrograms from all the classified fusion beats can be considered.

In another embodiment, other morphology features may be used to classify beats as capture or non-capture, such as the area under the curve or the slope of a portion an electrogram waveform. A fusion beat can then be reclassified as a capture beat if it meets at least one of the morphology feature requirements and there are a pre-determined number of fusion beats that demonstrate similar characteristics.

The device according to any of the embodiments described above may be programmed to perform a capture threshold procedure by successively decreasing the pacing energy of pacing pulses delivered to the cardiac site, classifying the recorded test electrogam recorded after each pacing pulse, and setting the capture threshold as the smallest pacing energy that achieves capture plus a specified safety margin. The device may be further programmed such that if: 1) the peak amplitude of the test electrogram has been found to have increased with decreasing pacing energy, 2) only one of the amplitude and location criteria is met, and 3) a predetermined number of immediately preceding test electrograms have been classified as representing fusion beats, a blanking/recharge parameter used to define a blanking interval for a sensing channel used to record the test electrogram is adjusted and/or the amplitude and/or timing criterion is modified.

Figure 3:
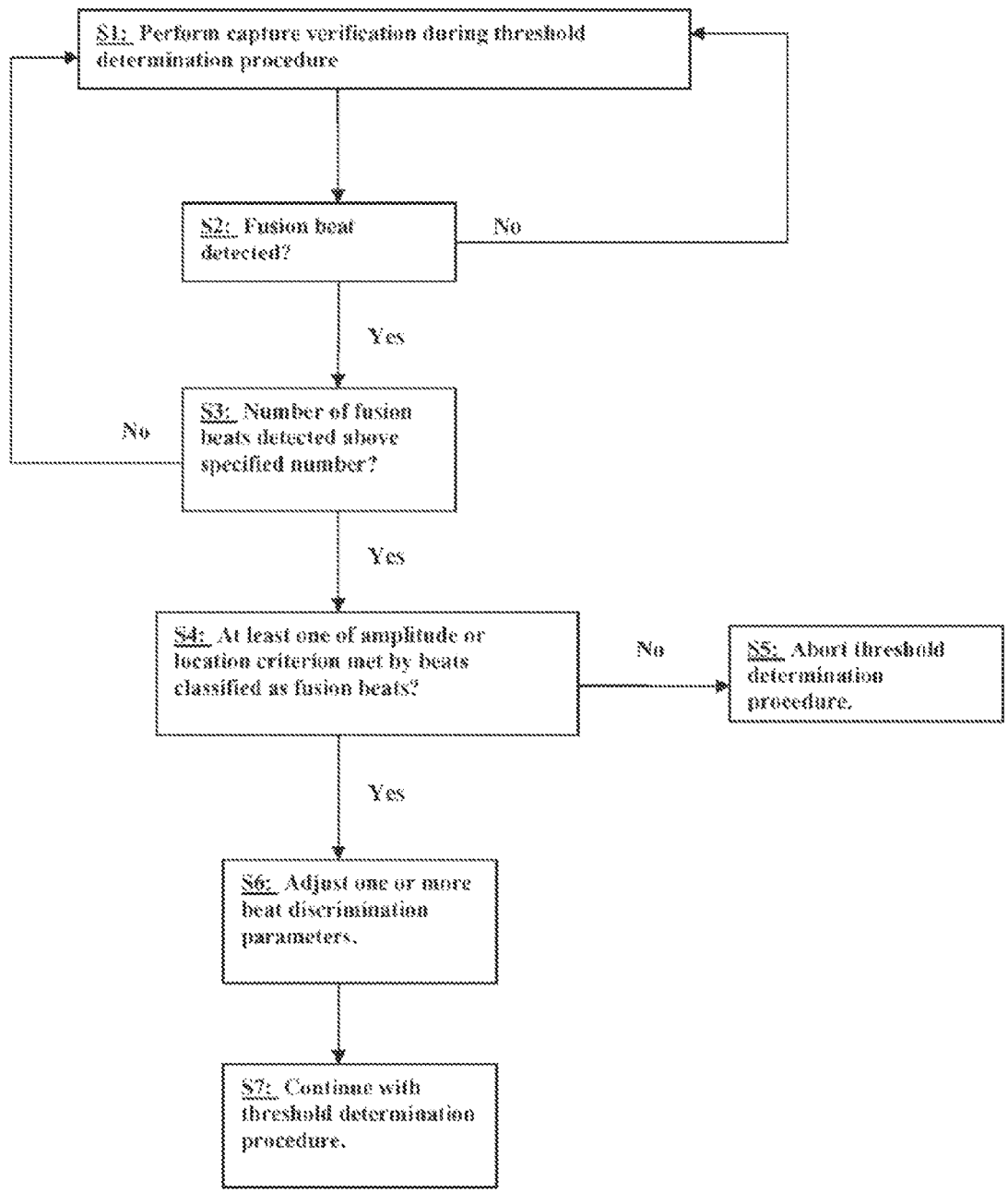
FIG. 3 illustrates an example algorithm that may be executed by the device controller during a capture threshold determination procedure.

FIG. 3 illustrates an example algorithm that may be executed by the device controller during a capture threshold determination procedure. At step S1, the device performs capture verification during a capture threshold determination procedure. If a fusion beat is detected at step S2, the threshold test is continued unless a predetermined number of such fusion beats have occurred as determined at step S3. At step S4, the device determines if at least one of amplitude or location criterion is met by beats classified as fusion beats. If not, the threshold determination procedure is aborted at step S5. Otherwise, one or more beat discrimination parameters such as described above are adjusted at step S6, and the threshold determination procedure is continued at step S7.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method for operating a cardiac rhythm management device, comprising:
 performing a capture threshold determination procedure by:
 delivering a pacing pulse to a cardiac site;
 recording a test electrogram after delivery of the pacing pulse;
 classifying the test electrogram as representing a capture beat, a fusion beat, or a non-capture beat;
 initiating delivery of pacing pulses with a pacing pulse energy that achieves capture and decreasing the pacing pulse energy of each successive pacing pulse until the lowest energy pacing pulse that results in a test electrogram classified as a capture beat is found, wherein test electrograms classified as fusion beats are disregarded;
 wherein the test electrogram is classified as a capture beat if the test electrogram meets both an amplitude criterion that specifies a peak amplitude and a location criterion that specifies a time window within which the peak amplitude must occur;
 wherein the test electrogram is classified as a non-capture beat if asystole is detected;
 wherein the test electrogram is classified as a fusion beat if it cannot be classified as either a capture beat or a non-capture beat; and,
 wherein the test electrogram is also classified as a capture beat if: 1) a non-zero number of immediately preceding test electrograms have been classified as fusion beats, and 2) the test electrogram meets only one of either the amplitude criterion or the location criterion.

2. The method of claim 1 further comprising, if only one of the amplitude and location criteria is met and a predetermined number of immediately preceding test electrograms have been classified as representing fusion beats, adjusting a blanking/recharge parameter used to define a blanking interval for a sensing channel used to record the test electrogram.

3. The method of claim 1 further comprising, if only one of the amplitude and location criteria is met and a predetermined number of immediately preceding test electrograms have been classified as representing fusion beats, modifying the amplitude criterion.

4. The method of claim 1 further comprising, if only one of the amplitude and location criteria is met and a predetermined number of immediately preceding test electrograms have been classified as representing fusion beats, decreasing the amplitude criterion.

5. The method of claim 1 further comprising, if only one of the amplitude and location criteria is met and a predetermined number of immediately preceding test electrograms have been classified as representing fusion beats, increasing the width of the time window specified by the location criterion.

6. The method of claim 1 further comprising, if: 1) the test electrogram exhibits a double peak, 2) only one of the amplitude and location criteria is met, and 3) a predetermined number of immediately preceding test electrograms have been classified as representing fusion beats, increasing the width of the time window specified by the location criterion to encompass the double peak.

7. A cardiac rhythm management device, comprising:
 pulse generation and sensing circuitry for connecting to electrodes and forming sensing and pacing channels;
 a controller for controlling the delivery of pacing pulses by the pulse generation circuitry and for receiving electrogram signals from the sensing circuitry;
 wherein the controller is programmed to:
 perform a capture threshold determination procedure by:
 delivering a pacing pulse to a cardiac site;
 recording a test electrogram after delivery of the pacing pulse;
 classifying the test electrogram as representing a capture beat, a fusion beat, or a non-capture beat;
 initiating delivery of pacing pulses with a pacing pulse energy that achieves capture and decreasing the pacing pulse energy of each successive pacing pulse until the lowest energy pacing pulse that results in a test electrogram classified as a capture beat is found, wherein test electrograms classified as fusion beats are disregarded;
 wherein the test electrogram is classified as a capture beat if the test electrogram meets both an amplitude criterion that specifies a peak amplitude and a location criterion that specifies a time window within which the peak amplitude must occur;
 wherein the test electrogram is classified as a non-capture beat if asystole is detected;
 wherein the test electrogram is classified as a fusion beat if it cannot be classified as either a capture beat or a non-capture beat; and,
 wherein the test electrogram is also classified as a capture beat if: 1) a non-zero number of immediately preceding test electrograms have been classified as fusion beats, and 2) the test electrogram meets only one of either the amplitude criterion or the location criterion.

8. The device of claim 7 wherein the controller is further programmed to, if only one of the amplitude and location criteria is met and a predetermined number of immediately preceding test electrograms have been classified as representing fusion beats, adjust a blanking/recharge parameter used to define a blanking interval for a sensing channel used to record the test electrogram.

9. The device of claim 7 wherein the controller is further programmed to, if only one of the amplitude and location criteria is met and a predetermined number of immediately preceding test electrograms have been classified as representing fusion beats, modify the amplitude criterion.

10. The device of claim 7 wherein the controller is further programmed to, if only one of the amplitude and location criteria is met and a predetermined number of immediately preceding test electrograms have been classified as representing fusion beats, decrease the amplitude criterion.

11. The device of claim 7 wherein the controller is further programmed to, if only one of the amplitude and location criteria is met and a predetermined number of immediately preceding test electrograms have been classified as representing fusion beats, increase the width of the time window specified by the location criterion.

12. The device of claim 7 wherein the controller is further programmed to, if: 1) the test electrogram exhibits a double peak, 2) only one of the amplitude and location criteria is met, and 3) a predetermined number of immediately preceding test electrograms have been classified as representing fusion beats, increase the width of the time window specified by the location criterion to encompass the double peak.

* * * * *